United States Patent [19]
Robie et al.

[11] Patent Number: 6,159,217
[45] Date of Patent: Dec. 12, 2000

[54] TROCHLEAR CLAMP

[76] Inventors: Bruce H. Robie, 7 Ashton Pl., Glen Rock, N.J. 07452; Jordan L. Ryalls, 736 Broadway, #10, New York, N.Y. 10003; John David Blaha, 440 Cypress St., Morgantown, W. Va. 26505; Thomas P. Sculco, 132 E. 95$^{th}$ St., New York, N.Y. 10128; Joseph D. Lipman, 531 E. 72$^{nd}$ St., Apt. 4B, New York, N.Y. 10021

[21] Appl. No.: 09/241,964

[22] Filed: Feb. 2, 1999

[51] Int. Cl.$^7$ .................................................. A61B 17/56
[52] U.S. Cl. ........................... 606/88; 606/207; 606/208; 81/424
[58] Field of Search ................................. 606/53, 86, 87, 606/88, 89, 205, 206, 207, 208; 433/159; 81/424, 424.5, 426, 426.5

[56] References Cited

U.S. PATENT DOCUMENTS

| | | | |
|---|---|---|---|
| 2,698,483 | 1/1955 | Berkowitz | 433/156 |
| 2,779,224 | 1/1957 | Coggburn | 175/4.53 |
| 2,794,253 | 6/1957 | Fitzsimmons . | |
| 3,964,352 | 6/1976 | Dukes | 81/426 |
| 4,424,035 | 1/1984 | Hansen . | |
| 5,098,436 | 3/1992 | Ferrante et al. . | |
| 5,258,032 | 11/1993 | Bertin . | |
| 5,474,559 | 12/1995 | Bertin et al. . | |
| 5,514,139 | 5/1996 | Goldstein et al. . | |
| 5,571,197 | 11/1996 | Insall . | |
| 5,601,563 | 2/1997 | Burke et al. . | |
| 5,665,090 | 9/1997 | Rockwood et al. . | |
| 5,697,933 | 12/1997 | Gundlapalli et al. | 606/96 |

FOREIGN PATENT DOCUMENTS 1600749  10/1990  U.S.S.R. .

OTHER PUBLICATIONS

Blakiston's, *New Gould Medical Dictionary* (1956) p. 889.
Bone Holding Forceps, Kirschner Medical Corporation, Jul. 1998, p. 10.
Bone Holding Forceps, Zimmer, Inc., Dec. 1991, p. A 326.

*Primary Examiner*—Michael Buiz
*Assistant Examiner*—David O. Reip
*Attorney, Agent, or Firm*—Darby & Darby

[57] ABSTRACT

A clamp device, cutting guide, and clamp slider used together in preparation to cutting of the distal end of the femur bone during total knee replacement surgery. The clamp device includes an upper arm and a lower arm rotatably secured to one another in a scissor-like manner. A curved movable component is rotatably secured to the proximal end of the lower arm. The clamp device is positioned around a portion of the distal end of the femur bone so that the distal end of the upper arm grasps a posterior ridge of the femur bone and the movable component of the lower arm is positioned along the contour of the deepest part of the trochlear groove, thereby defining a plane through the deepest part of the trochlear groove of the femur bone. Next, a clamp slider is removably secured to a cutting guide so that channels defined in the clamp slider and cutting guide are substantially aligned with one another. The assembled clamp slider and cutting guide are then slid over the clamp and rotated until the clamp is received in the channels with the cutting guide in contact with an anterior portion of the femur bone. Then the cutting guide is positioned so that arms projecting from each side are substantially aligned with a center of the medial or lateral epicondyle of the femur bone. Lastly, the clamp slider and clamp are removed, whereby the cutting guide remains properly aligned on the femur bone in order to ensure the correct angle of the cuts in the femur bone.

7 Claims, 11 Drawing Sheets

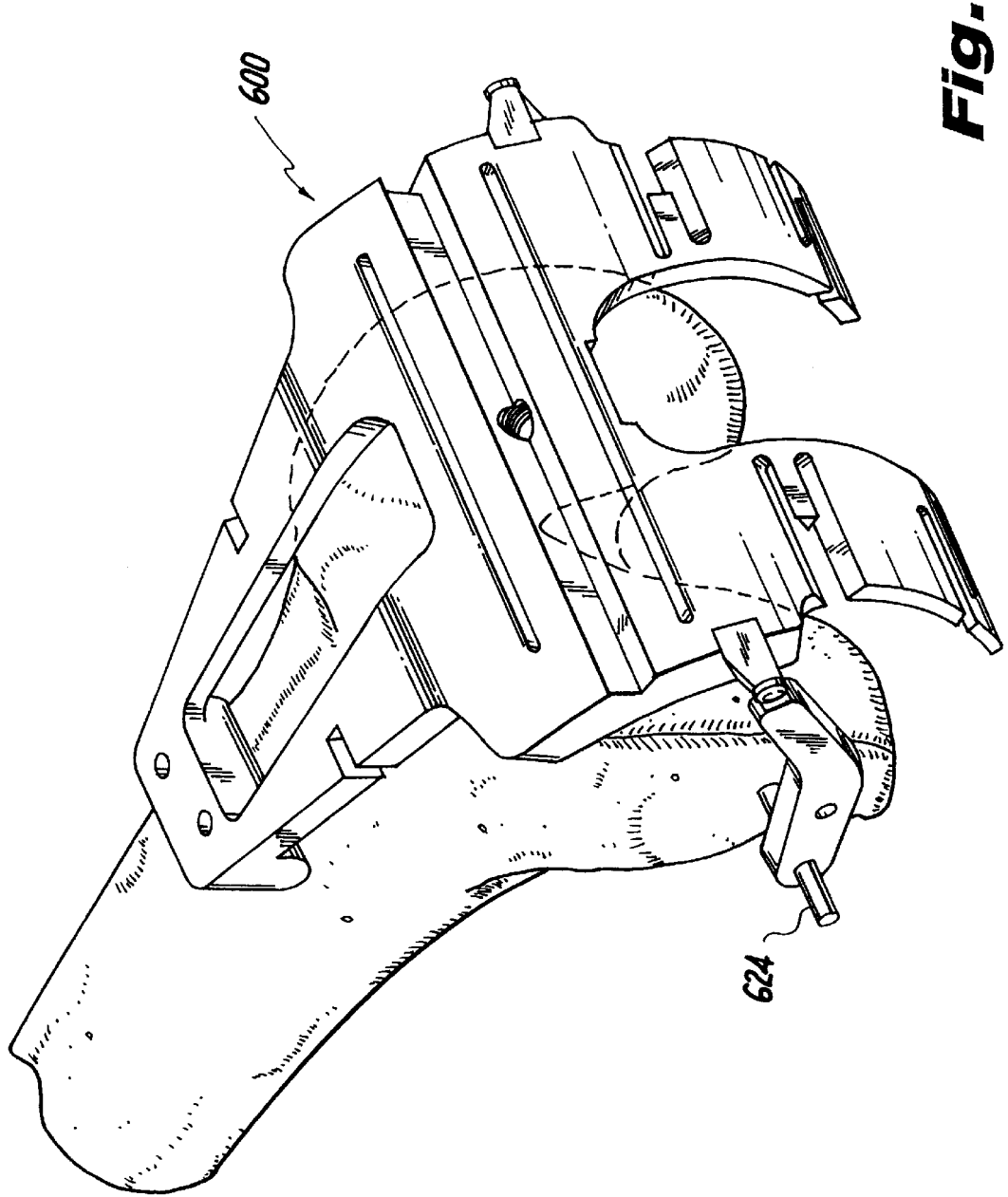

TROCHLEAR CLAMP

BACKGROUND OF THE INVENTION

1. Field of the Invention

The present invention relates to an instrument and method for accurately aligning cuts in a femur bone during Total Knee Replacement (TKR) surgery, and in particular to a trochlear clamp that allows positioning of the femoral component relative to the trochlear groove.

2. Description of Related Art

A total knee replacement or prosthesis, substitutes for a patient's arthritic or otherwise dysfunctional natural knee joint. The prosthesis offers the patient an alternative treatment for the chronic pain and discomfort often associated with such problems.

Burstein et al. U.S. Pat. No. 4,298,992 illustrates a widely used total knee joint prosthesis known as the Insall-Burstein (I/B) knee. Such prostheses comprise a femoral component which is attached to the patient's femur, a tibial component attached to the patient's tibia, and a patellar component attached to the patient's patella. To use this prosthesis, it is necessary to shape by resection the patient's femur, tibia and patella. The tibia and patella are shaped by a flat cut. In the case of the I/B prosthesis, the femoral component requires five cuts in the distal end of the femur. These cuts conform to complementary portions of the femoral component which engage the bone. It is important that these femoral cuts be precisely located to insure the patient's natural anatomic limb alignment and normal anatomical movement.

It is therefore desirable to develop an instrument for properly positioning a cutting guide to ensure the accuracy in the location of the five cuts in the femur bone.

SUMMARY OF THE INVENTION

An object of the present invention is to provide an instrument for use in precisely locating the position of the femoral component prior to performing the cuts during TKR surgery.

It is another object of the invention to provide a device for shaping the distal surface of a femur preparatory to implanting a knee prosthesis, wherein all of the cuts required to shape the femur can be made using a single instrument.

Historically, surgeons have used extramedullary alignment to orient the instruments to cut the distal femur. The present locating instrument references the trochlear groove (sulcus) of the distal femur and the medial or lateral epicondyle thereby locating the cutting instrument relative to established femoral anatomy to ensure that the knee prosthesis works in concert with the ligaments of the knee.

The present invention is directed to a combination for creating cuts in a femur bone relative to the epicondylar axis for use in total knee replacement surgery. In accordance with the present invention, the combination includes a clamp device used to located a plane through the deepest part of a trochlear groove, a cutting guide, and a clamp slider. The cutting guide has a first channel and at least one cutting slot defined therein, and is curved to complement the anatomical contour of the distal end of the femur bone. A second channel is defined in the slider. The clamp slider is removably secured to the cutting guide with the first and second channels substantially aligned for receiving the clamp device in the first and second channels thereby limiting movement of the cutting guide to substantially the plane defined by the clamp device.

In addition, the present invention is directed to a method of shaping a patient's femur bone having a trochlear groove preparatory to implanting a knee prosthesis using the device described above. Initially, a proximal end of a clamping device having an upper arm and a lower arm is positioned around a portion of the trochlear groove with the proximal end of the upper arm grasping a posterior ridge of the femur bone. Then, the upper and lower arms of the clamping device are squeezed together in a fixed position around the trochlear groove of the femur bone.

BRIEF DESCRIPTION OF THE DRAWINGS

The foregoing and other features of the present invention will be more readily apparent from the following detailed description and drawings of illustrative embodiments of the invention wherein like reference numbers refer to similar elements throughout the several views and in which:

FIG. 3b is a cross-sectional view of the movable component along lines 3b—3b in FIG. 3a;

FIG. 3c is a cross-sectional view of the movable component along lines 3c—3c in FIG. 3a;

FIG. 15 is a perspective view of the cutting guide in accordance with the present invention properly positioned in the trochlear groove of the femur bone after the clamp device and clamp slider have been removed.

DETAILED DESCRIPTION OF THE INVENTION

Figure 1:
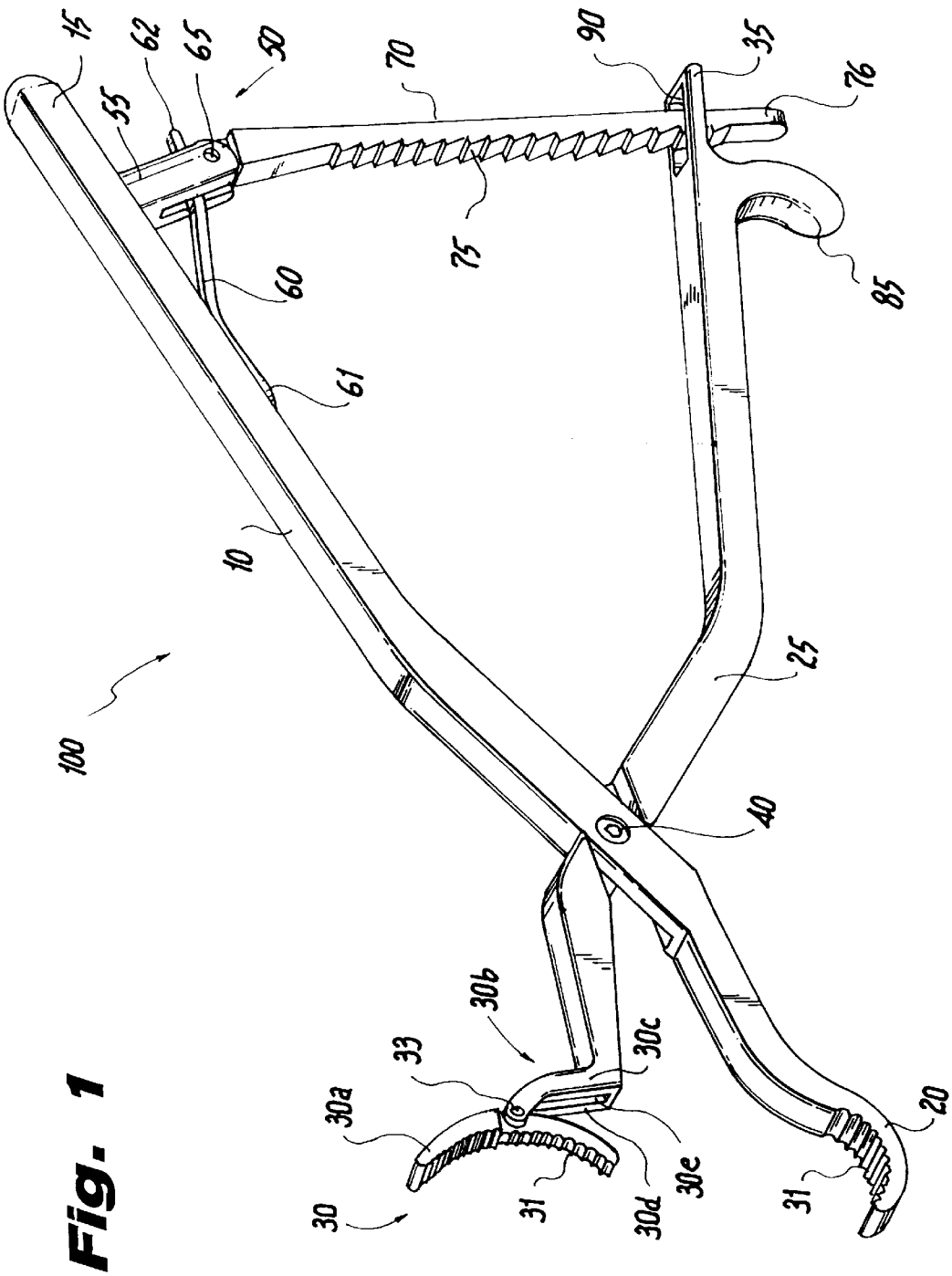
FIG. 1 is a front perspective view of the trochlear clamp in accordance with the present invention.

The trochlear clamp instrument 100 shown in FIG. 1 is used to properly position a cutting guide relative to the trochlear groove prior to making any incisions in the femur bone. It has been recognized that the plane formed through the deepest or bottom part of the trochlear groove is substantially perpendicular to the epicondylar axis. In addition, it has been determined that the epicondylar axis may be used as a reference when orienting a femoral component on the femur and, thus when making the cuts in the femur bone prior to orientation of the femoral component of the prosthesis. The clamp device in accordance with the present invention is used to define the plane formed at the bottom of the trochlear groove and limit placement of the cutting guide to movement only in that plane thereby facilitating installation of the femoral component during THR surgery.

In particular, the trochlear clamp 100 includes an upper arm 10 and a lower arm 25. Upper arm 10 comprises a fixed curved proximal end 20 and a distal end 15, whereas the lower arm 25 includes a curved proximal end 30, which is freely rotatable to accommodate varying sized femur bones of different patients, and a distal end 35. In a preferred embodiment a curved finger support member 85 is disposed proximate to the distal end 35 of the lower arm 25 for supporting the surgeon's hand while clamping down on the femur bone. The upper and lower arms 10, 25 are hinged together about a pin 40 and operate similar to that of a scissors.

Figure 2:
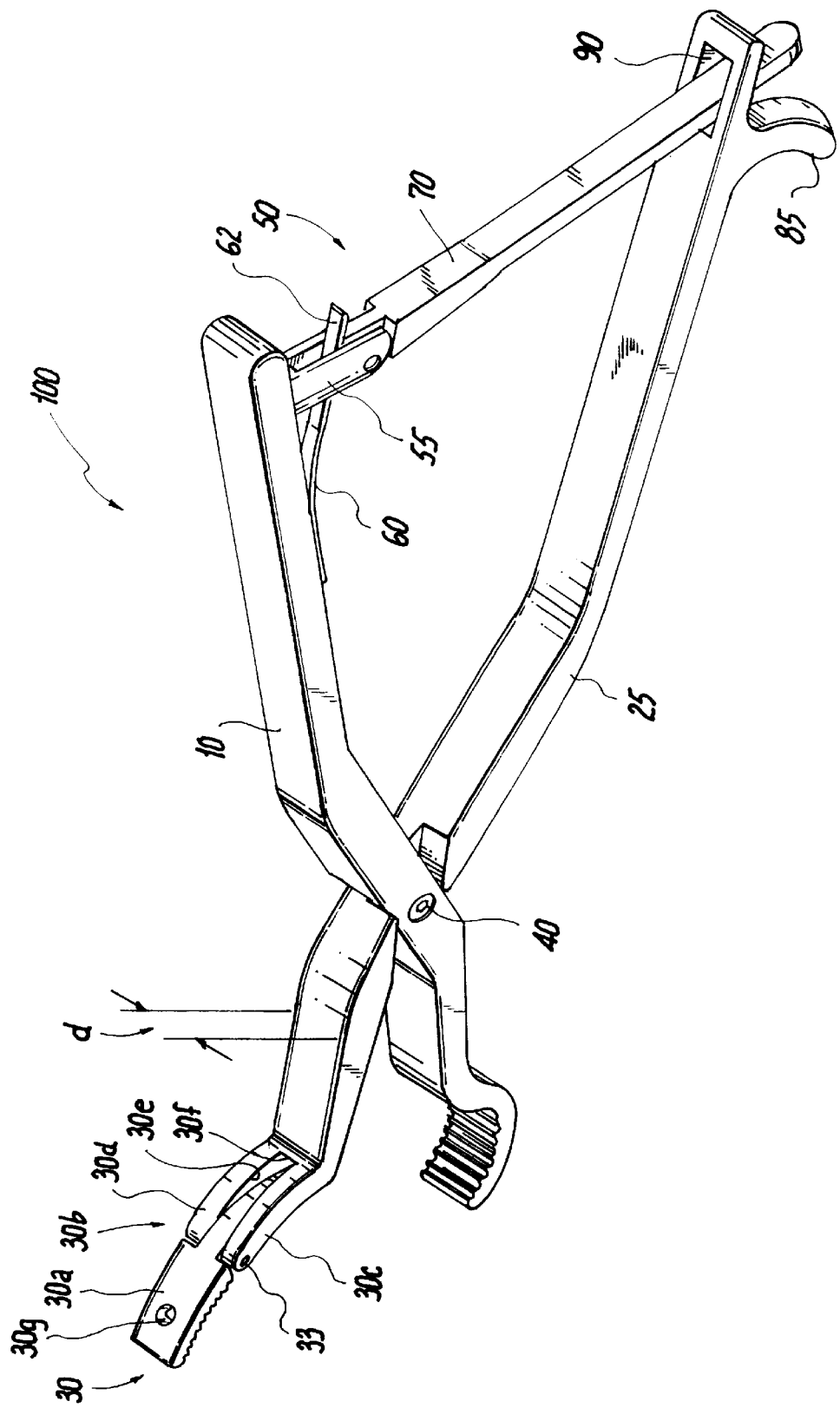
FIG. 2 is a rear perspective view of the trochlear clamp of FIG. 1.

Proximal end 20 is preferably integral to the upper arm 10. On the other hand, the upper proximal end 30 comprises two components, a fixed component 30b integral to the lower arm 25 and a movable component 30a hinged thereto about a pin 33 disposed at approximately the lowest point of the curve. FIG. 2 shows a rear perspective view of the clamping device. The fixed component 30b of the proximal end 30 of the lower arm 25 terminates in two prongs 30c, 30d with a channel 30e defined therebetween. A bore is defined in the end of each prong 30c, 30d for receiving the pin 33. The interior width of the channel 30e is substantially equal to the outer width of the movable component 30a, and the length of each prong 30c, 30d is substantially equal to the length from the pin 33 to the end of the narrow lower half of the movable component 30a so that the movable component is freely rotatable therebetween. The base of the channel is angled to prevent the narrow lower half of the movable component 30a, when rotated in a counter-clockwise direction, from passing through the channel 30e, whereas in a clockwise direction rotation of the moveable component 30a is restricted by the wide upper half as it contacts the outer surface of the prongs 30c, 30d. In addition, an aperture 30g may be defined in the wide upper half of the movable component 30a. Once the clamping device is properly positioned in the trochlear groove a pin may be inserted through the aperture 30g to maintain the clamping device in place.

Figure 3A:
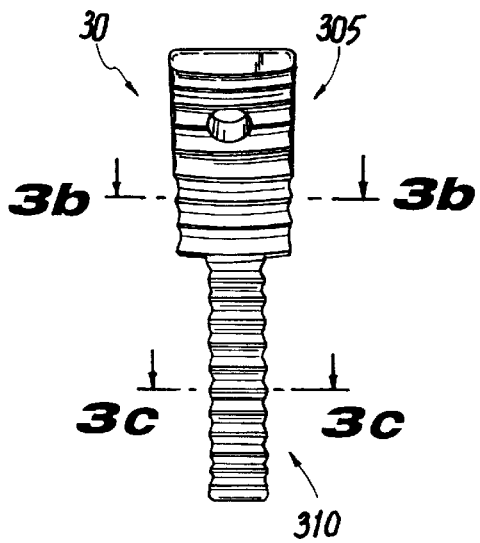
FIG. 3a is a front plan view of the movable component of the trochlear clamp of FIG. 1.
Figure 3B:
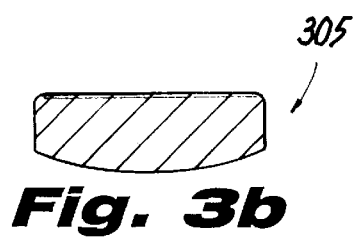
Figure 3C:
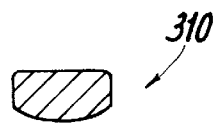

In a preferred embodiment, traction, such as grooved recesses or raised projections, is provided along the inner surface of the lower and upper proximal ends 20, 30 to substantially prevent or reduce slippage while grasping the femur bone with the clamp device 100. FIG. 3a shows the T-shape of the movable component 30a with its wide upper half 305 and narrow lower half 310. As shown in FIGS. 3b and 3c, the inner surface of the upper and lower halves of the movable component that contact the trochlear groove preferably are convex in a direction perpendicular to the concave curvature of the movable component to assist in grasping the femur bone during clamping.

Figure 4:
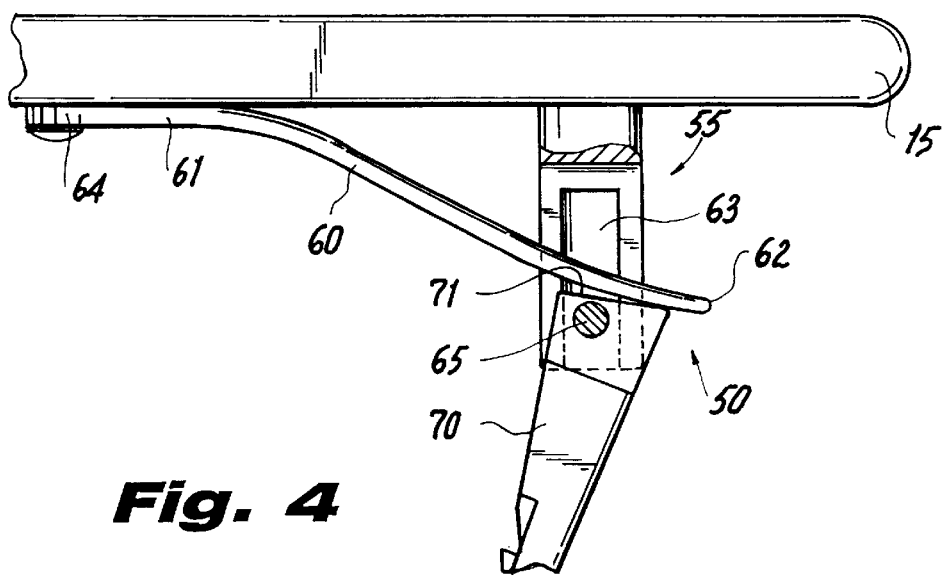
FIG. 4 is a partial cross-sectional view of the upper arm, base, tensioning member, and pivoting end of the ratchet of the trochlear clamp of FIG. 1.

As shown in FIGS. 1, 2 and 4, a rachet mechanism 50 is arranged proximate the distal end of the trochlear clamp 100 for securing in place the upper arm 10 relative to the lower arm 25, once the two arms have been properly positioned around the femur bone. The rachet mechanism 50 includes a U-shaped base 55 projecting substantially perpendicularly from and mounted to the lower surface of the upper arm 10 proximate its distal end. A hole is defined in each end of the U-shaped base 55 for receiving a pin 65. Ratchet 70 has a substantially planar pivoting end 71 and a hole defined therein proximate that end. The ratchet 70 is interposed between the ends of the U-shaped base 55 and pivots about a pin 65 inserted through the ends of the U-shaped base and the hole in the ratchet. A tensioning member 60 is mounted at one end 61 to the inner surface of the upper arm 10, while its opposite free end 62 passes through the U-shaped base 55 and imparts a force on a distal portion of the pivoting end 71 thereby causing the ratchet 70 to pivot about pin 65 towards the proximal end of the clamp. A series of teeth 75 facing the proximal end of the clamp are disposed along a portion of the side of the ratchet 70 between the pivoting end 71 and its opposite free end 76. In a preferred embodiment each tooth has a triangular cross-section.

Figure 5:
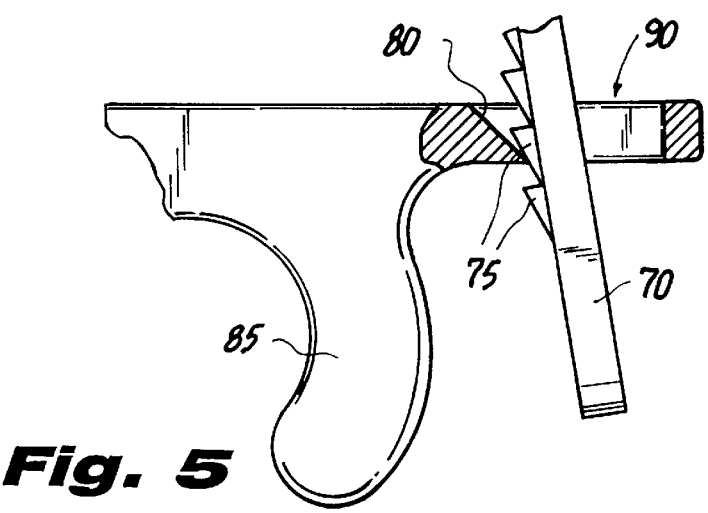
FIG. 5 is a partial cross-sectional view of the lower arm and free end of the ratchet of the trochlear clamp of FIG. 1.

The free end 76 of the ratchet extends through a rectangular opening 90 in the distal end of the lower arm 25. As shown in the enlarged view in FIG. 5, a catch 80 is disposed in the interior surface of the aperture 90 along a lateral edge closest to the proximal end of the clamp. The tensioning member 60 imparts a force on distal portion of the pivoting end 71 of the ratchet 70 causing it to rotate in a clockwise direction towards the proximal end of the clamp. As the clamp is squeezed about the femur bone the teeth 75 pass one-by-one through the aperture and engage the catch 80. Catch 80 permits movement only in a downward direction, thereby preventing the user from opening the clamp wider. To release the upper arm from around the femur bone the free end 76 of the ratchet is pulled towards the distal end of the clamp until the teeth 75 disengage and clear the catch 80.

Figure 6:
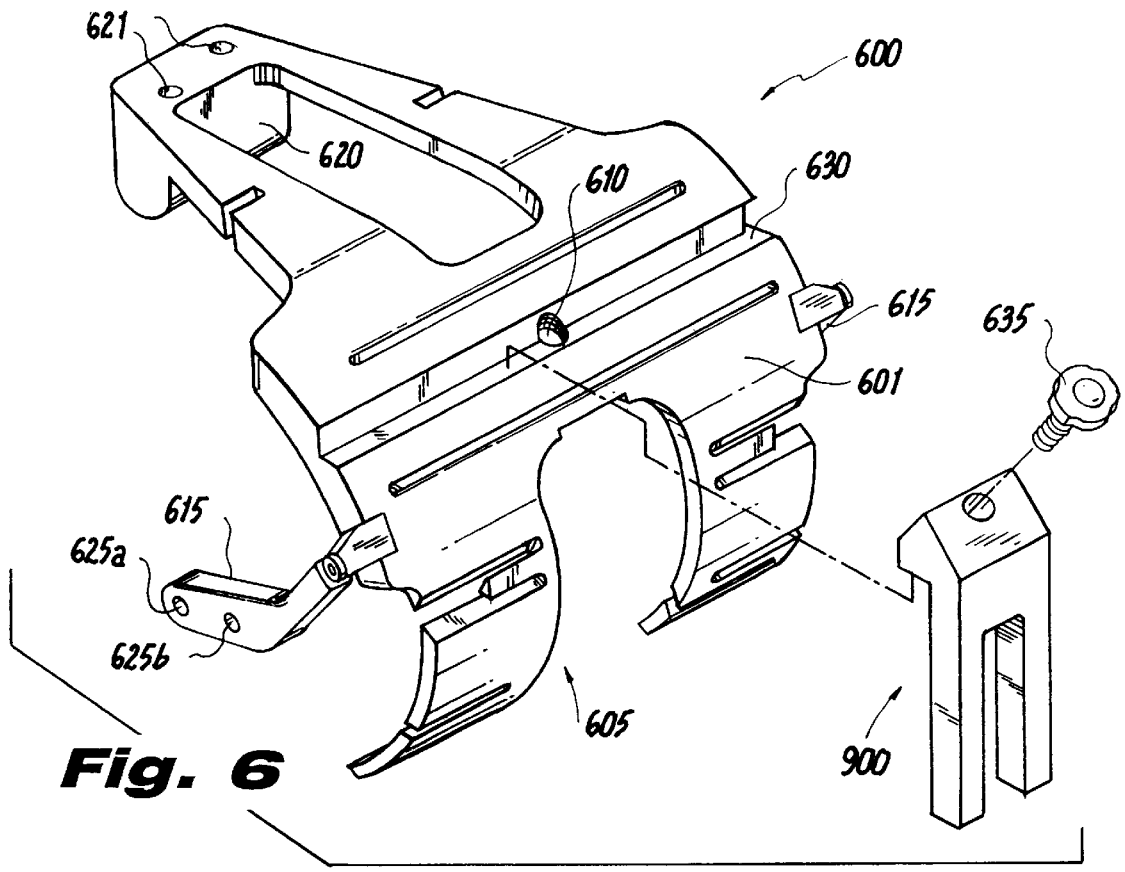
FIG. 6 is an exploded view of the cutting guide and clamp slider in accordance with the present invention.
Figure 7:
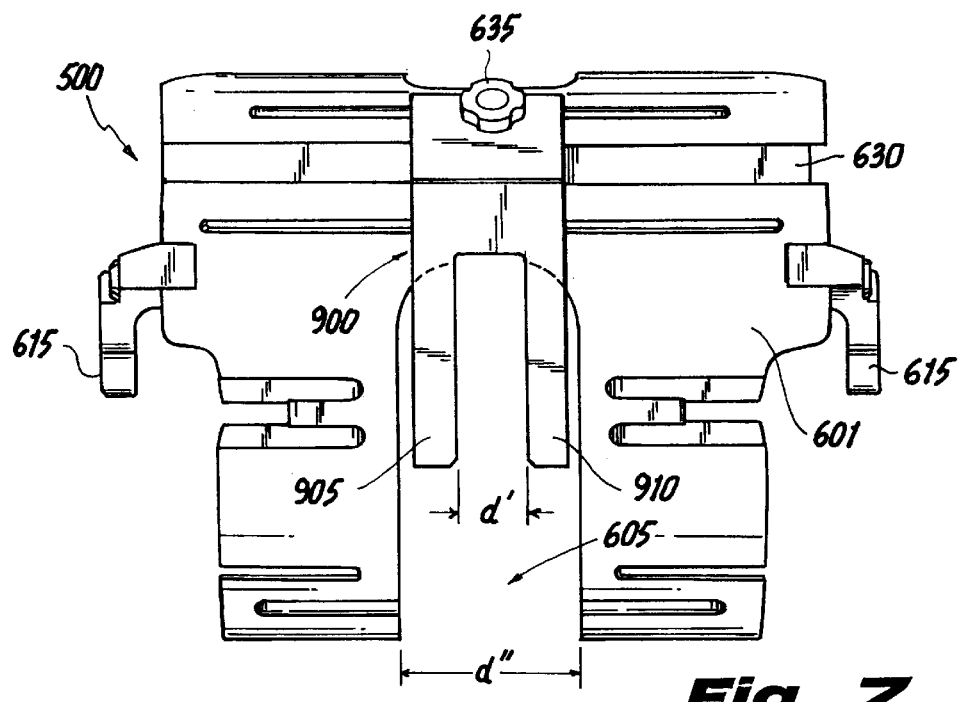
FIG. 7 is a view of the assembled cutting guide and clamp slider of FIG. 6.
Figure 8:
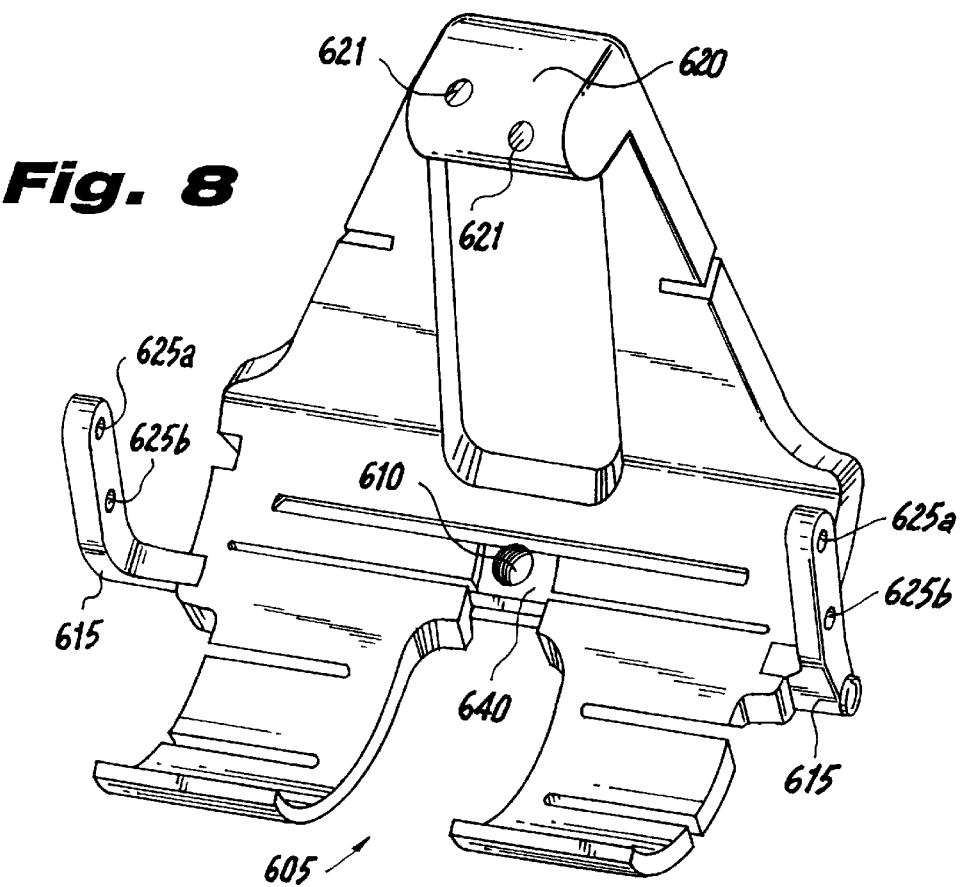
FIG. 8 is a view of the interior surface of the cutting guide in accordance with the present invention.

FIGS. 6–8 show a preferred embodiment of the cutting guide 600 that is curved to complement the anatomical contour of the distal end of the femur bone. In particular, FIG. 8 shows the inner surface, that is, the surface in contact with the femur bone, of the cutting guide, whereas FIGS. 6 and 7 show the outer surface of the cutting guide. Specifically, the cutting guide has a base 601 curved to complement the anatomical contour of the distal end of the patient's femur bone and a U-shaped recess 605 substantially centered in a lateral direction defined therein. An arm 615 projects from each side of the base 601. The cutting guide 600 is positioned with the femur bone interposed between the two projecting arms 615. A section of the inner surface of the cutting guide 600 proximate the closed end of the recess 605 is cut away to form a tapered section 640, to provide clearance when the clamp is removed from the femur bone, as described further below. Tapered section 640 provides sufficient clearance so that the clamp device 100 may be removed posteriorly from the femur bone once the cutting guide 600 has been properly aligned and secured to the femur bone, as described in detail below. After the cutting guide has been properly positioned on the femur bone, pins 624 are inserted through the holes 625a defined in each projecting arm 615. In a preferred embodiment, a second pair of holes 625b may be defined in each arm to provide additional fixation if necessary. It is, however, contemplated and within the intended scope of the invention to provide more than two pairs of holes in each arm. A supporting member 620 is disposed on an end of the cutting guide opposite that of the U-shaped recess. In a preferred embodiment, holes 621 are defined through the supporting member 620 through which pins are received to secure the cutting guide to the femur bone. When the cutting guide is properly positioned the supporting member rests 620 on the femur bone. In a preferred embodiment, a substantially right angle channel 630 extends laterally across at least a portion of the cutting guide and intersects a hole 610 defined in the cutting guide, which is substantially centered in a lateral direction. Other configurations of the cutting guide are contemplated and within the intended scope of the invention, such as the cutting guide described in International Patent Application No. PCT/US98/01655, filed on Jan. 27, 1998, herein incorporated by reference.

Figure 9:
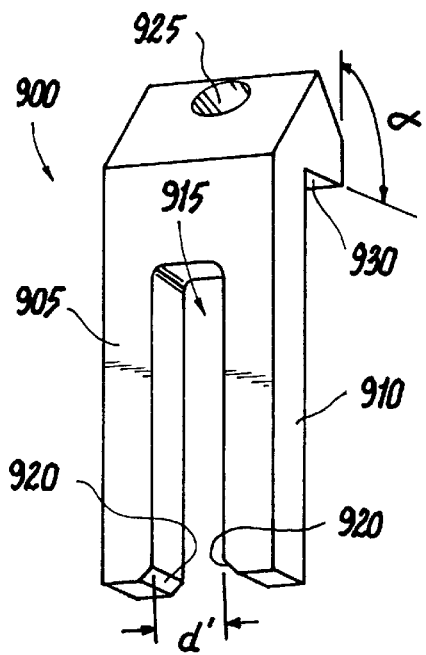
FIG. 9 is a perspective view of the clamp slider in accordance with the present invention.

A fork-shaped clamp slider 900 is shown in FIGS. 6, 7 and 9. One end of the clamp slider 900 terminates in two substantially parallel projecting prongs 905, 910 which are displaced from one another thereby defining a channel 915 therebetween. In a preferred embodiment, the interior corner of each projecting prong 920 is chamfered to assist in insertion of the proximal end of the clamp device through the channel 915. The outer width d of the upper half 305 of the proximal end 30 of the trochlear clamp is substantially equal to the inner width d' of the channel 915 for insertion therein. In addition, the inner width d' of the channel 915 is slightly smaller than the inner width d" of the channel 605 of the cutting guide. A perspective view of the clamp slider in accordance with a preferred embodiment is shown in FIG. 9. The clamp slider has an angle α substantially equal to 90 degrees to complement that of channel 630. An opening 925 is defined at an angle in the clamp slider and extends through the edge 930 for receiving a thumb screw to secure the clamp slider 900 to the cutting guide 600.

FIG. 7 is a perspective view of the assembled device 500 including the clamp slider 900 and cutting guide 600. During assembly the clamp slider 900 is positioned on the outer surface of the cutting guide 600 by inserting edge 930 into channel 630 and aligning the respective holes 610 and 925, with one another. A thumb screw 635 is inserted into the aligned holes 610 and 925 to secure the two devices together.

Figure 10:
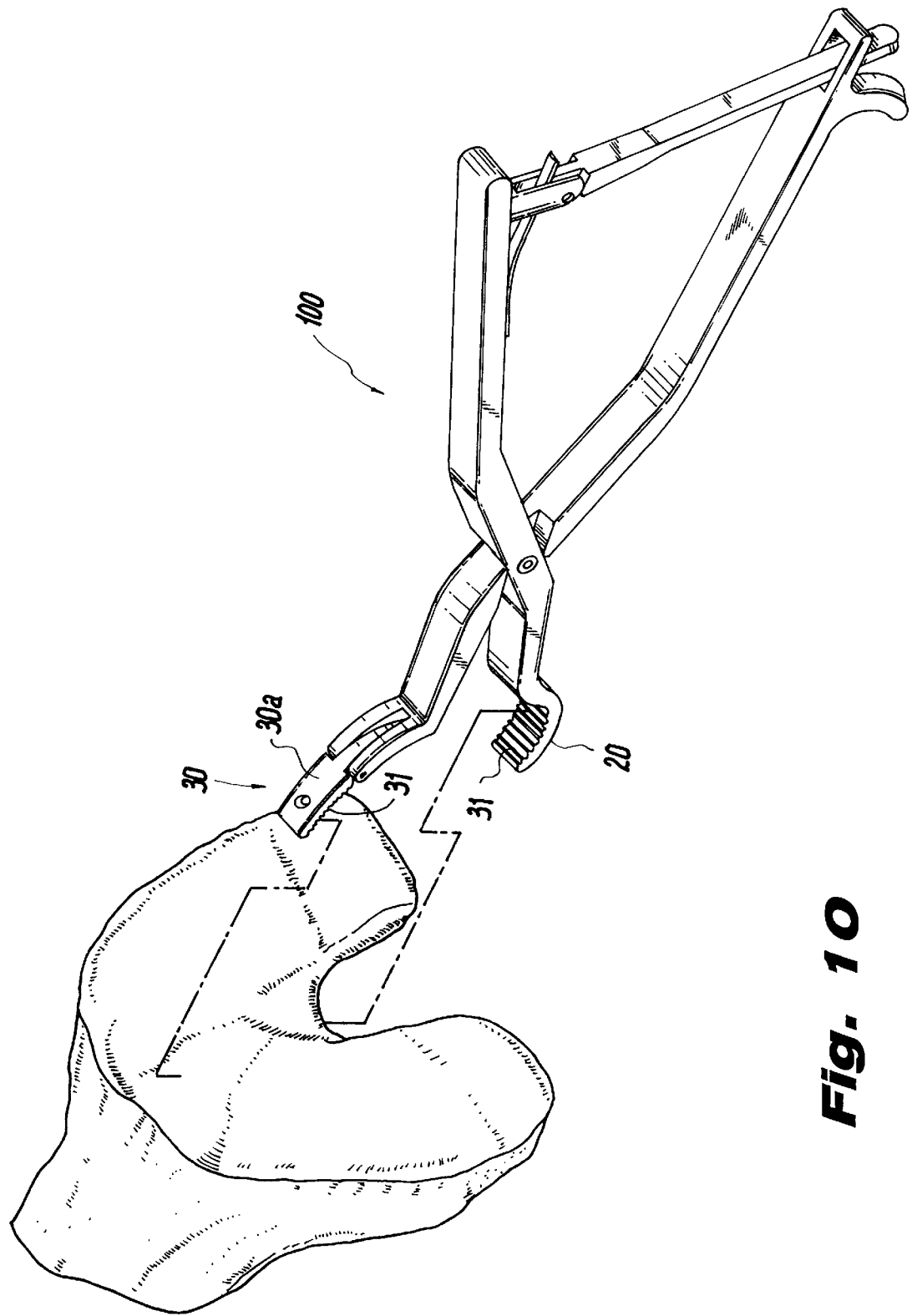
FIG. 10 is an exploded view showing the clamp device prior to positioning in the deepest part of the trochlear groove of the distal end of the femur bone.
Figure 11:
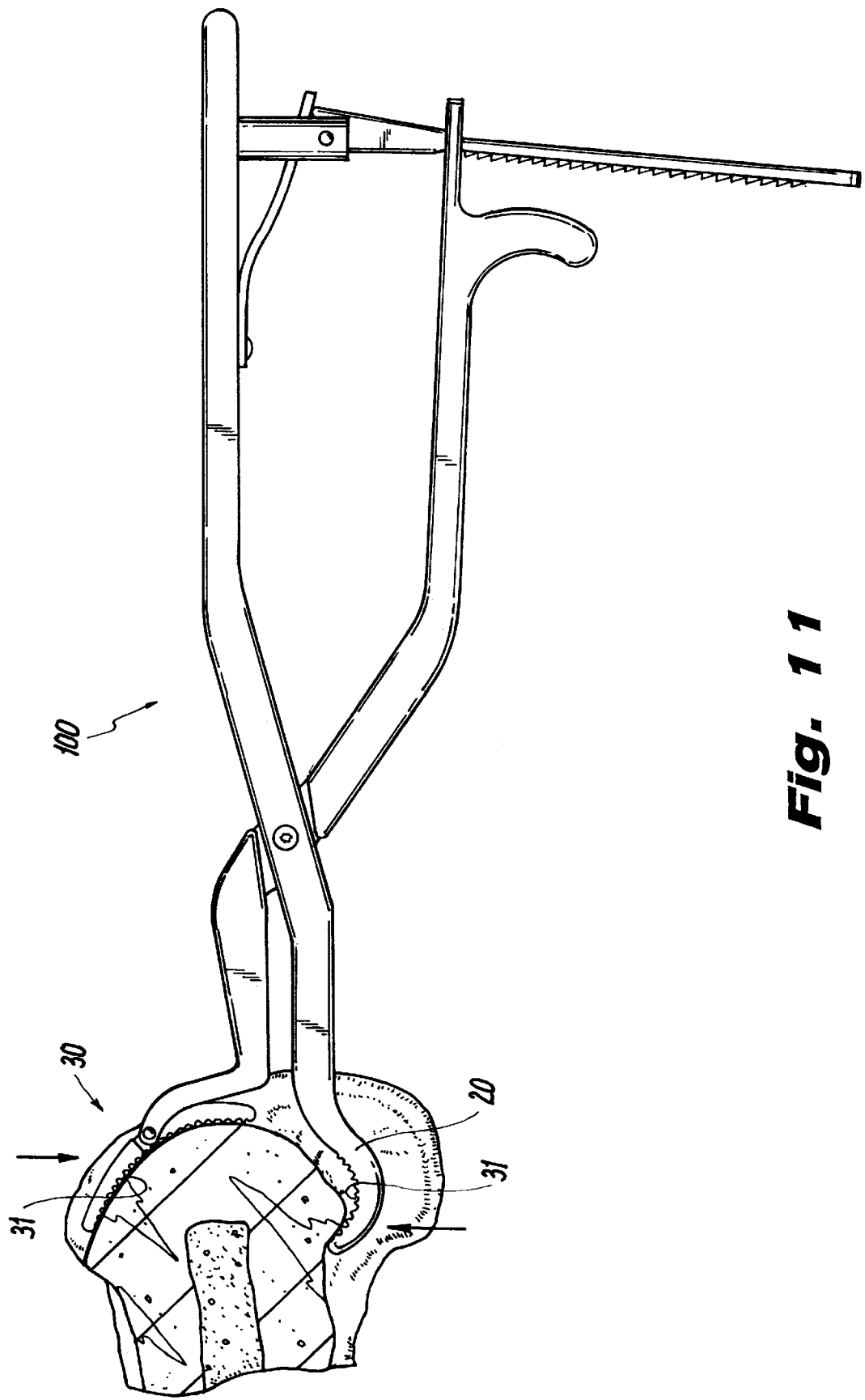
FIG. 11 is a partial cross-sectional view of the clamp device in accordance with the present invention properly positioned in the deepest part of the trochlear groove of the distal end of the femur bone.

During surgery the surgeon positions the proximal end of the clamp device around a portion of the trochlear groove of the femur bone, as shown in FIGS. 10 and 11. Specifically, the surgeon reaches posteriorly on the femur with the proximal end 20 of the upper arm 10 and grasps the posterior ridge of bone 700 located between the posterior condyles and proximate to the epicondylar axis, while positioning the proximal end 30 of the lower arm 25 along the top of the trochlear groove. As the upper and lower arms 10, 25, respectively, are squeezed together the proximal end 30 pivots about pin 33 until it positions itself to complement the contour of the trochlear groove. Simultaneously, the free end of the ratchet 70 extends downward through the opening 90 of the lower arm 25 and, in turn, the teeth 75 engage the catch 80 thereby preventing or substantially reducing movement in an opposite (upward) direction. This is advantageous in that if the surgeon lets go of the clamping device, it maintains its fixation on the femur bone. When the clamp device is properly positioned and clamped around a portion of the trochlear groove the surgeon may insert a pin through hole 30g and into the femur bone to further secure the clamp in place. At this point in time the clamp device defines a plane formed through a spline drawn along the deepest part of the trochlear groove.

Figure 12:
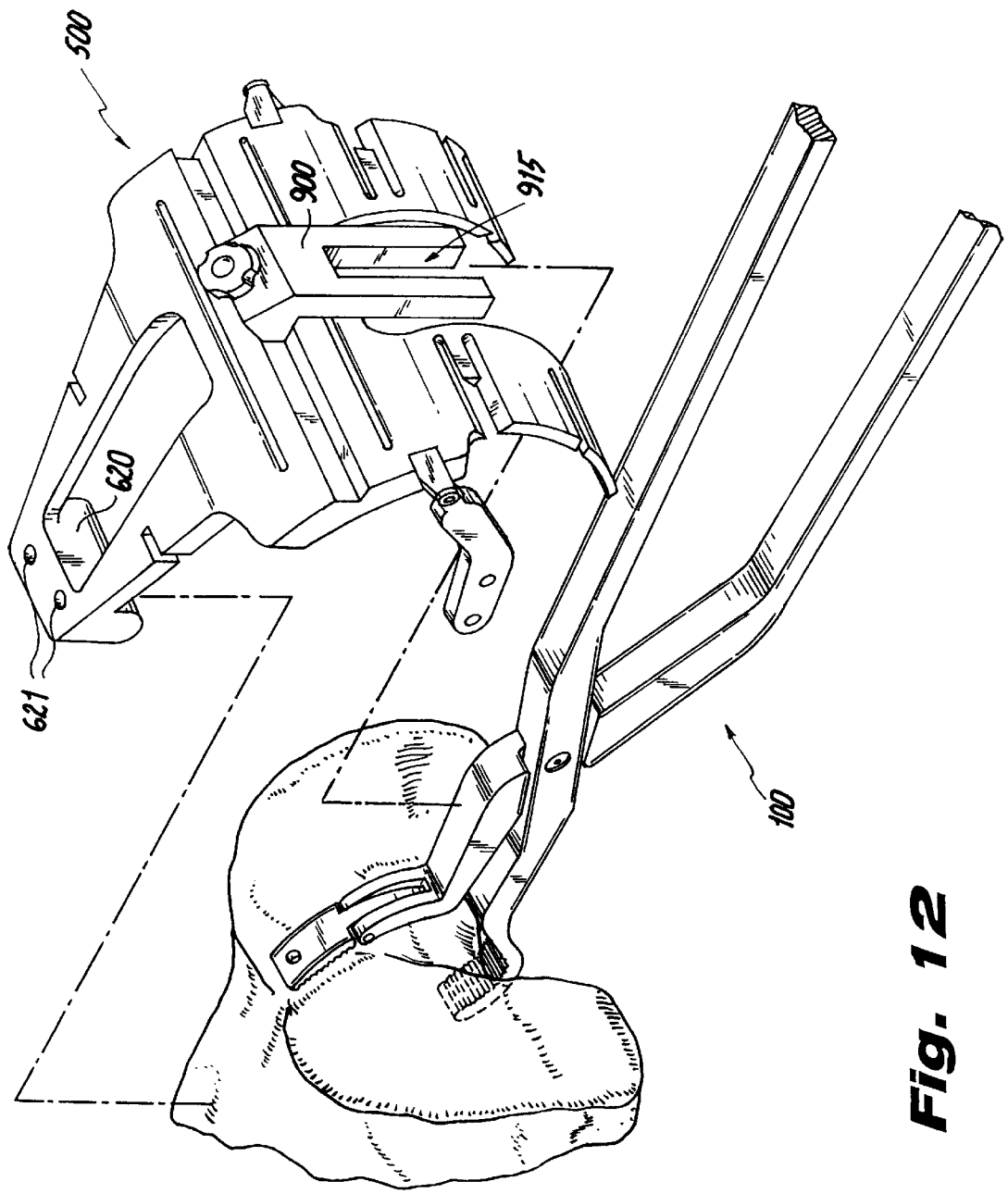
FIG. 12 is an exploded view of the clamp device positioned in the deepest part of the trochlear groove of the distal end of the femur bone prior to placement of the assembled cutting guide and clamp slider.
Figure 13:
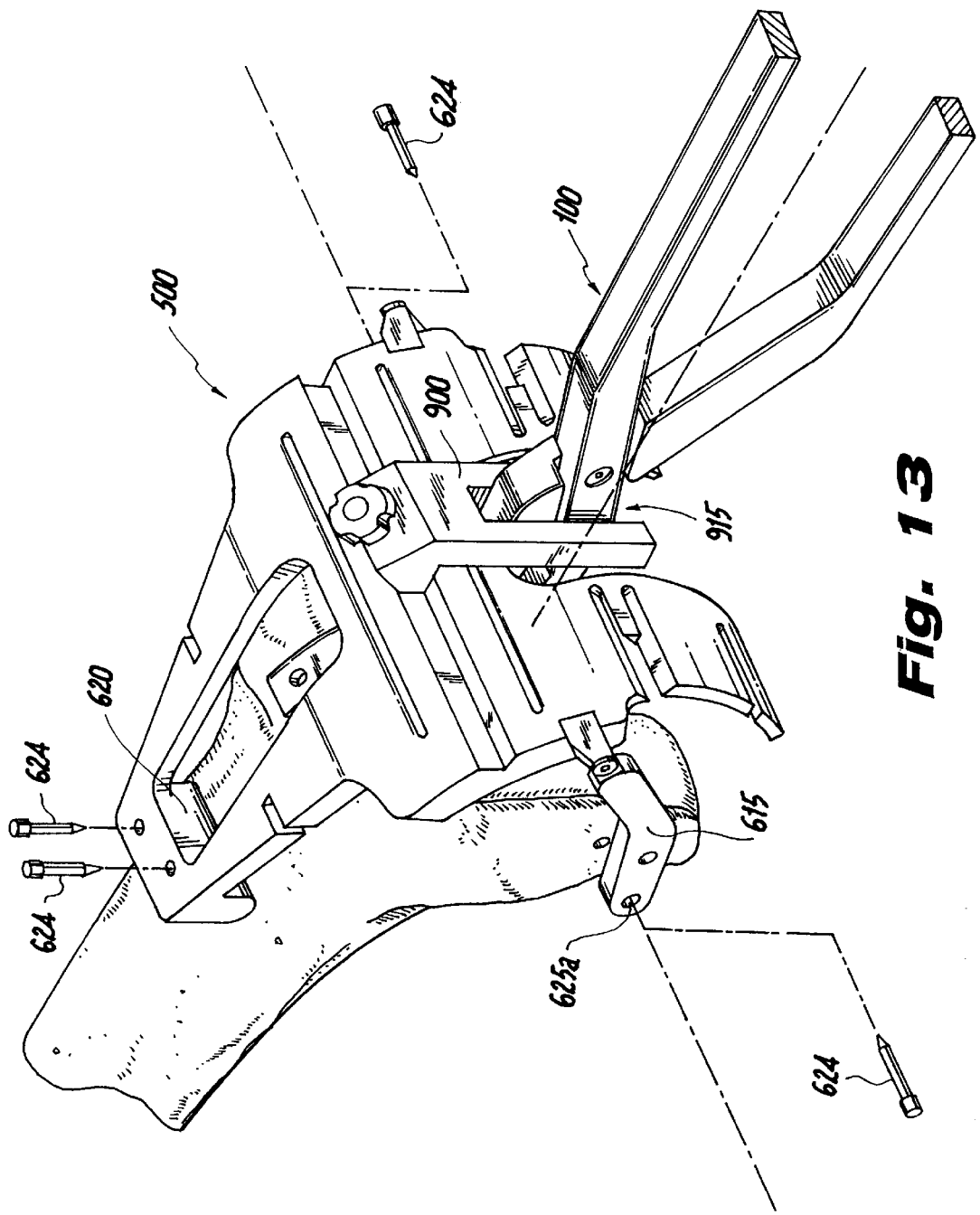
FIG. 13 is a perspective view of the cutting guide, clamp slider and clamp device properly positioned on the distal end of the femur bone.
Figure 14:
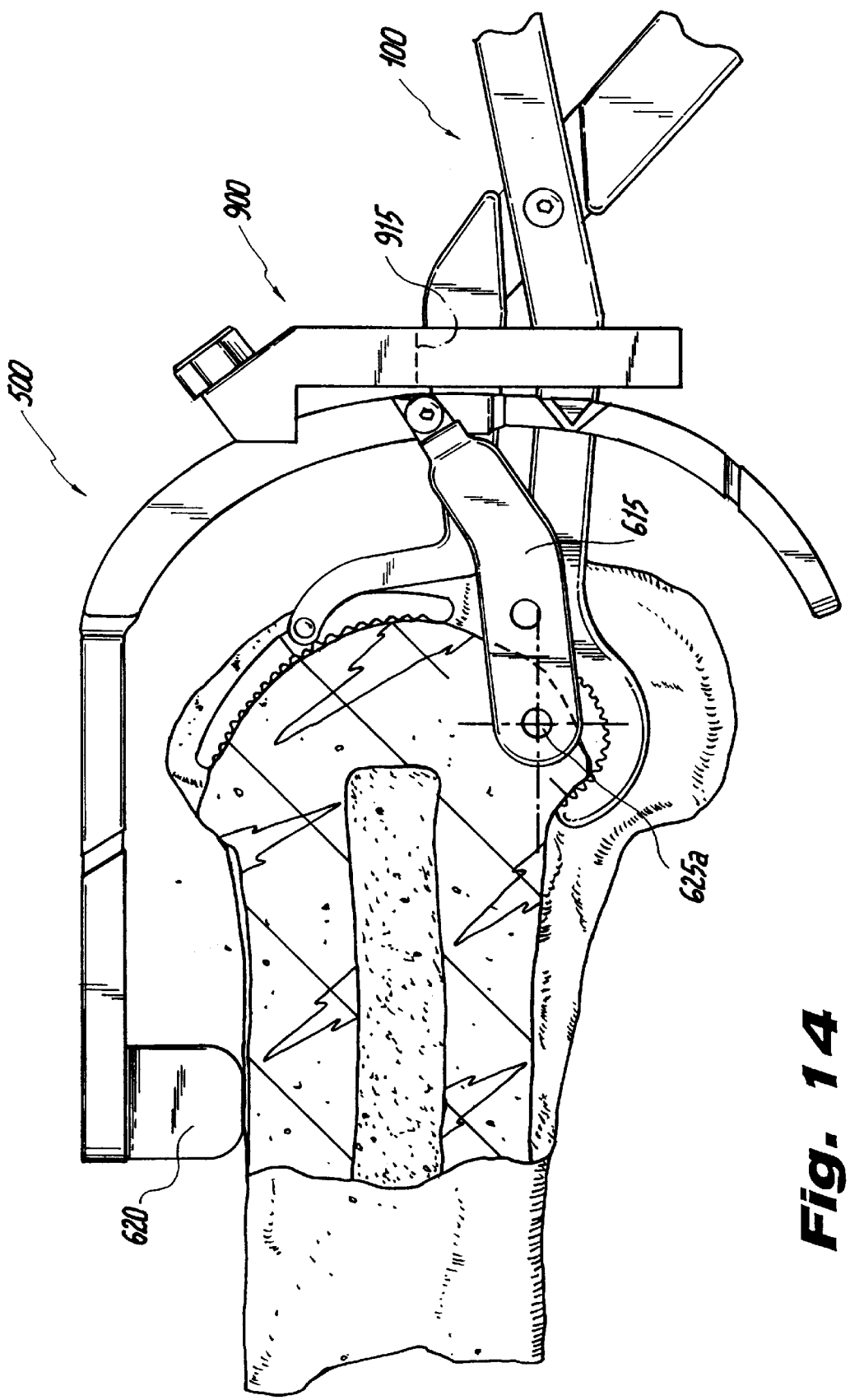
FIG. 14 is a side view of the cutting guide, clamp slider and clamp device of FIG. 13 with a cross section of the distal end of the femur bone along a plane defined by the deepest part of the trochlear groove.

After the clamp device has been properly positioned and clamped around a portion of the trochlear groove of the femur bone, the surgeon slides the assembled device 500 (including the clamp slider 900 and cutting guide 600) around the clamp device 100, as shown in FIG. 12. Then the assembled device 500 is rotated until the clamp device 100 is received in the channel 915. The inner width d' of the channel 915 is substantially equal to the outer width d of the proximal end of the clamp. Thus, the clamp device 100 restricts movement of the assembled device 500 to translation in the plane formed through a spline drawn along the deepest part of the trochlear groove, and rotation about a longitudinal axis through the assembled device perpendicular to said plane. The surgeon rotates the assembled device until the stopping member 620 rests on the anterior aspect of the femur bone. While maintaining stopping member 620 in contact with the anterior aspect of the femur bone, the assembled device is translated and rotated until the free end of the projecting arms 615 are substantially aligned with the center of the medial or the lateral epicondyle of the femur, as shown in FIGS. 13 and 14. The device is now aligned along the epicondylar axis. When the assembled device has been properly positioned, the surgeon inserts pins through one of the pair of holes 625a or 625b, and through hole 621 to secure the assembled device in place. Thereafter, the surgeon detaches the clamp slider 900 by unscrewing the thumb screw 635 and removes the clamp device 100 posteriorly from the femur bone, leaving the cutting guide 600 secured to the femur bone, as shown in FIG. 15. As previously described, the tapered section 640 provides sufficient clearance so that the proximal end 30 of the clamp device 100 may be removed from around the femur bone while the cutting guide 600 remains fixed thereto. The cutting guide is now properly positioned on the femur bone thereby ensuring that the slits defined therein, through which the cuts are made to the femur bone, are substantially parallel to the epicondylar axis. The cuts in the femur bone are made by inserting a cutting device directly into the slots defined in the cutting guide.

In an alternative embodiment, the apparatus in accordance with the present invention may be used in conjunction with an attachment device having slots defined therein. Once the cutting guide has been properly aligned and the clamp device and clamp slider have been removed, the attachment device is placed over the outer surface of the cutting guide with the slots of the two devices substantially aligned, and the two devices are secured to one another. The cuts in the femur bone are made by inserting a cutting device into the slots defined in the attachment and cutting guide. In this alternative embodiment, the attachment device lengthens the slot thereby further refining the precision of the angle of the cuts.

Thus, while there have been shown, described, and pointed out fundamental novel features of the invention as applied to preferred embodiments thereof, it will be understood that various omissions, substitutions, and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A trochlear clamp for locating a plane through a deepest part of a trochlear groove of a femur bone, comprising:

an upper arm having a curved proximal end;

a lower arm having a proximal end, said lower arm being rotatably secured to said upper arm; and a curved movable component rotatably secured to the proximal end of said lower arm and having an inner surface adapted to contact said trochlear groove of the femur bone, the inner surface being convex in a direction substantially perpendicular to a concave curvature of said movable component.

2. A trochlear clamp in accordance with claim 1, wherein said lower arm has a hole defined therein proximate the distal end.

3. A trochlear clamp in accordance with claim 2, further comprising:

a releasable locking ratchet mechanism for maintaining in a fixed postion said upper arm relative to said lower arm, said releasable locking ratchet mechanism comprising:

a U-shaped base projecting from said upper arm and defining a channel;

a ratchet having a fixed end rotatably secured to said base and an opposite free end passing through the hole defined in the distal end of said lower arm; and a tensioning member inserted through the channel of said base and contacting said fixed end of said ratchet, said tensioning member imparting a torque on said ratchet projecting the free end of said ratchet towards the proximal end of said lower arm.

4. A trochlear clamp in accordance with claim 1, wherein said movable component is divided into an upper section having a predetermined width and a lower section narrower in width relative to said upper section.

5. A trochlear clamp in accordance with claim 1, wherein the proximal end of said lower arm terminates in two prongs defining a U-shaped channel therebetween having an inner width substantially equal to an outer width of the lower section of said movable component.

6. A trochlear clamp in accordance with claim 1, further comprising traction means disposed on the inner surface of the curved proximal end of said upper arm and said movable component.

7. A trochlear clamp in accordance with claim 6, wherein said traction means is one of grooved recesses and raised projections.

* * * * *